United States Patent [19]

Sugita et al.

[11] Patent Number: 4,997,984

[45] Date of Patent: Mar. 5, 1991

[54] PROCESS FOR PREPARATION OF N-(α-ALKOXYETHYL)-CARBOXYLIC ACID AMIDE

[75] Inventors: Shuichi Sugita; Tetsuo Kudo; Kuniomi Marumo, all of Oita, Japan

[73] Assignee: Shawa Denko K.K., Tokyo, Japan

[21] Appl. No.: 452,936

[22] Filed: Dec. 19, 1989

[51] Int. Cl.$^5$ ............... C07C 233/00; C07C 235/00; C07C 237/00; C07C 239/00

[52] U.S. Cl. .................... 564/183; 564/182; 564/217; 564/224

[58] Field of Search ............. 564/224, 217, 182, 183

[56] References Cited

U.S. PATENT DOCUMENTS

| 2,742,501 | 4/1956 | Kleine et al. ............... 564/224 |
| 4,554,377 | 11/1985 | Stackman et al. ........... 564/205 |

FOREIGN PATENT DOCUMENTS

| 0251118 | 1/1988 | European Pat. Off. ......... 564/224 |
| 62-289549 | 12/1962 | Japan . |
| 50-76014 | 6/1975 | Japan . |
| 55-154589 | 12/1980 | Japan . |
| 56-75464 | 6/1981 | Japan . |
| 60-149551 | 8/1985 | Japan . |
| 63-96160 | 4/1988 | Japan . |
| 2152929 | 8/1985 | United Kingdom ............ 564/224 |

*Primary Examiner*—Glennon H. Hollrah
*Assistant Examiner*—S. C. Rand

*Attorney, Agent, or Firm*—Sughrue, Mion, Zinn, Macpeak & Seas

[57] ABSTRACT

A process for the preparation of an N-(α-alkoxyethyl)-carboxylic acid amide represented by the following formula [I]:

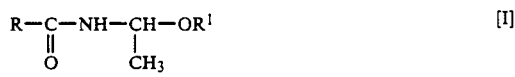

wherein R stands for a hydrogen atom, an alkyl group having 1 to 6 carbon atoms, a benzyl group or an aryl group, and $R^1$ stands for an alkyl group having 1 to 10 carbon atoms or a cycloalkyl group, which comprises reacting an ethylidene-bisamide represented by the following formula [II]:

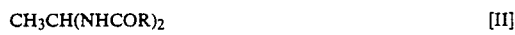

wherein R stands for a hydrogen atom, an alkyl group having 1 to 6 carbon atoms, a benzyl group or an aryl group, with an alkanol in the presence of an acid catalyst. According to this process, a high-purity N-(α-alkoxyethyl)carboxylic acid amide, which is valuable as an intermediate for the production of an N-vinylcarboxylic acid amide and the like, can be easily prepared from cheap and easily available starting materials.

6 Claims, No Drawings

PROCESS FOR PREPARATION OF N-(α-ALKOXYETHYL)-CARBOXYLIC ACID AMIDE

BACKGROUND OF THE INVENTION

1. Field of the Invention

The present invention relates to a process for the preparation of an N-(α-alkoxyethyl)carboxylic acid amide, which is an intermediate leading to an N-vinylcarboxylic acid amide which can be utilized as the material for the synthesis of polyvinylamine as a water-soluble polymer, and chemicals such as taurine and cysteamine. More particularly, the present invention relates to a process for preparing an N-(α-alkoxyethyl)carboxylic acid amide by reacting an ethylidene-bisamide with an alkanol in the presence of an acid catalyst.

2. Description of the Related Art

Various processes for the synthesis of an N-(α-alkoxyethyl)carboxylic acid amide have been proposed. For example, the following processes can be mentioned.

(a) Japanese Unexamined Patent Publication No. 50-76014 discloses a process in which N-acyl-α-alanine is subjected to electrolytic oxidation in an alcoholic solvent to effect decarboxylation and alkoxylation.

(b) Japanese Unexamined Patent Publication No. 55-154589 discloses a process in which an N-ethylcarboxylic acid amide is subjected to electrolytic oxidation in an alcoholic solvent to effect alkoxylation.

(c) Japanese Unexamined Patent Publication No. 56-75464 discloses a process in which an α-halogenoalkyl ether is reacted with a carboxylic acid amide in the presence of a tertiary amine.

(d) The specification of U.S. Pat. No. 4,554,377 discloses a process in which dimethylacetal is reacted with a carboxylic acid amide in the presence of an acid catalyst.

(e) Japanese Unexamined Patent Publication No. 60-149551 discloses a process in which an N-(α-alkoxyethyl)carboxylic acid amide is prepared through N-(α-hydroxyethyl)formamide obtained from formamide and acetaldehyde.

All of these known processes however, have serious disadvantages. For example, the processes (a) and (b) are disadvantageous in that the starting N-acyl-α-alanine and N-ethylcarboxylic acid amide are expensive, production is difficult because an electrochemical method is used, and a problem arises in the maintenance and control of an electrolytic cell and electrodes.

In the process (c), for the synthesis of the starting α-halogenoalkyl ether, a hydrogen halide must be used in an amount equimolar to the starting aldehyde.

The process (d) is defective in that dimethylacetal must be separately synthesized, and be once isolated and used. In the process (e), the starting carboxylic acid amide is limited to formamide giving a relatively stable N-(α-hydroxyethyl) compound.

For example, N-(α-hydroxyethyl)acetamide which is the intermediate formed when acetamide is used as the starting compound is an unstable compound, and isolation of this compound is impossible. The same reaction that occurs when formamide is used, cannot be advanced.

As apparent from the foregoing description, none of the conventional processes for the synthesis of an N-(α-alkoxyethyl)carboxylic acid amide can be regarded as widely-applicable and simple process.

As the process for industrially advantageously preparing an N-(α-alkoxyethyl)carboxylic acid amide while solving the problems of these conventional processes, the present inventors proposed a process comprising reacting three easily available and cheap compounds, i.e., a carboxylic acid amide, acetaldehyde, and an alcohol, in one state in the presence of a strongly acidic or weakly acidic cation-exchange resin, to synthesize an N-(α-alkoxyethyl)carboxylic acid amide at a high yield [see Japanese Unexamined Patent Publication No. 62-289549 (Laid-open on Dec. 16, 1987) and Japanese Unexamined Patent Publication No. 63-96160 (Laid-open on Apr. 27, 1988)].

According to this process, the intended N-(α-alkoxyethyl)carboxylic acid amide can be obtained at a high yield in one stage by using three easily available starting materials, and cumbersome post treatments such as a separation of the catalyst are not necessary. According to this process, the intended N-(α-alkoxyethyl)carboxylic acid can be simply obtained at a high yield, but the acetaldehyde and alcohol must be used in excessive amounts relative to the carboxylic acid amide and the acetaldehyde and alcohol must be recovered after the reaction and reused.

SUMMARY OF THE INVENTION

A primary object of the present invention is to overcome the defects of the conventional processes, such as the low availability of the starting materials, economical disadvantages and narrow application range, and the defects of the process previously proposed by the present inventors, such as the need to recover and recycle excess starting materials, and to provide a process in which an intended N-(α-alkoxyethyl)carboxylic acid amide can be simply prepared at a high yield by reacting an ethylidene-bisamide, which is easily prepared from easily available cheap compounds, i.e., acetaldehyde and a carboxylic acid amide, or a vinyl ether and a carboxylic acid amide, with an alkanol.

More specifically, in accordance with the present invention, the above-mentioned object can be attained by a process for the preparation of an N-(α-alkoxyethyl)carboxylic acid amide represented by the following formula [I]:

wherein R stands for a hydrogen atom, an alkyl group having 1 to 6 carbon atoms, a benzyl group or an aryl group, and $R^1$ stands for an alkyl group having 1 to 10 carbon atoms or a cycloalkyl group which comprises reacting an ethylidene-bisamide represented by the following formula [II]:

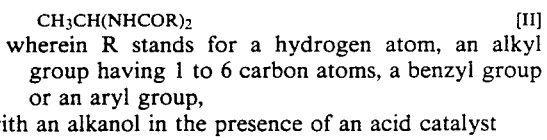

wherein R stands for a hydrogen atom, an alkyl group having 1 to 6 carbon atoms, a benzyl group or an aryl group,
with an alkanol in the presence of an acid catalyst

DESCRIPTION OF THE PREFERRED EMBODIMENTS

The ethylidene-bisamide used as the starting material in the present invention can be easily synthesized by a reaction between acetaldehyde and a carboxylic acid amide, a reaction between acetal and a carboxylic acid amide, a reaction between a vinyl ether and a carboxylic acid amide or a reaction between a vinyl ester and a carboxylic acid amide, as is well-known in the art (see, for example, Organic Reactions, 14, pages 247–261). Nevertheless, the reactions of the ethylidene-bisamide have seldom been studied, and especially, the reaction of the ethylidene-bisamide with an alkanol has not been clarified. The present inventors carried out an investigation of this reaction of the ethylidene-bisamide with an alkanol, not heretofore studied, and as a result, found that the intended N-(α-alkoxyethyl)carboxylic acid amide can be obtained at a high yield under mild reaction conditions in the presence of an acid catalyst. The present invention is based on this finding.

Either a homogeneous catalyst or a heterogeneous catalyst can be used as the acid catalyst in the present invention. As the homogeneous acid catalyst, there can be mentioned, for example, mineral acids such as sulfuric acid, hydrochloric acid and nitric acid, and organic acids such as methane-sulfonic acid and p-toluene-sulfonic acid. As the heterogeneous acid catalyst, there can be mentioned, for example, an acidic cation exchange resin.

The ethylidene-bisamide used in the present invention includes, for example, bisamides derived from acetaldehyde and an aliphatic carboxylic acid amide such as formamide, acetamide, propionamide or α-phenylacetamide, and bisamides derived from acetaldehyde and an aromatic carboxylic acid amide such as benzamide. Ethylidene-bisacetamide is most preferable.

An aliphatic alcohol and an alicyclic alcohol are generally used as the starting alkanol in the present invention, and an alkanol having 1 to 10 carbon atoms is preferably used. For example, there can be mentioned methanol, ethanol, n-propyl alcohol, isopropyl alcohol, n-butyl alcohol, sec-butyl alcohol, n-amyl alcohol, iso-amyl alcohol, neopentyl alcohol, cyclopentanol, n-hexanol, cyclohexanol, n-octanol, iso-octanol, 2-ethylhexanol and n-decanol. Among these alkanols, methanol, ethanol, n-propyl alcohol, isopropyl alcohol, n-butyl alcohol, n-amylalcohol, n-hexanol and 2-ethylhexanol are especially preferable, and isopropanol, n-butyl alcohol and n-amylalcohol are most preferable. An alkanol having 11 carbon atoms or more can be used for the reaction with he ethylidene-bisamide, but the boiling points and melting points of the alkanol and N-(α-alkoxyethyl)carboxylic acid amide become high and it becomes difficult to isolate and purify the intended product, and thus the use of such a higher alkanol is not practically preferable.

The ratio between the ethylidene-bisamide and alkanol is selected from the range of from 1/1 to 1/50 (molar ratio), and is preferably in the range of from $\frac{1}{2}$ to 1/30 (molar ratio). If the molar ratio is lower than this range, the conversion of the ethylidene-bisamide is reduced, and if the molar ratio is higher than this range, no improvement of the conversion or selectivity can be expected and the process becomes economically disadvantageous.

The reaction temperature is generally selected from the range of from 0° C. to 300° C., and a reaction temperature of 10° C. to 200° C. is preferable. If the reaction temperature is too low, the reaction speed is drastically reduced, and if the reaction temperature is too high, a side reaction occurs in the formed N-(α-alkoxyethyl)-carboxylic acid amide, resulting in a reduction of the selectivity. An optimum reaction temperature depends on the kind and amount of the acid catalyst used and the composition of the starting materials. Also, an optimum reaction time depends on the reaction conditions. Accordingly, to obtain the intended N-(α-alkoxyethyl)carboxylic acid amide at a high yield, it is important to set the reaction temperature and reaction time appropriately according to the reaction conditions actually adopted. The reaction pressure is not particularly critical, and the reaction can be carried out under a reduced pressure, atmospheric pressure or elevated pressure.

After the reaction, the catalyst is neutralized if necessary, and the reaction mixture is concentrated, distillated, extracted and the like to obtain a substantially pure intended N-(α-alkoxyethyl)carboxylic acid amide or a solution thereof.

Of these post treatments, an appropriate post treatment is selected while taking the physical properties of the intended N-(α-alkoxyethyl)carboxylic acid amide, the starting ethylidene-bisamide and the carboxylic acid amide formed as the by-product into consideration.

Sometimes the unreacted ethylidene-bisamide is precipitated as a crystal after completion of the reaction, and accordingly, the ethylidene-bisamide can be recovered by filtration before the post treatment described above.

Where an aliphatic alcohol having 1 to 4 carbon atoms is used as the alkanol, since the boiling point of the intended N-(α-alkoxyethyl)carboxylic acid amide is relatively low, the intended product can be easily recovered by distillation. In this case, also the carboxylic acid amide formed as the by-product is recovered by distillation. Of course, a method can be adopted in which the excess alcohol is removed from the reaction mixture by distillation under a reduced pressure, an organic solvent and water are added to the residue, and the mixture is thoroughly shaken to extract the N-(α-alkoxyethyl)carboxylic acid amide into the organic layer. In this method, the unreacted ethylidene-bisamide and the carboxylic acid amide formed as the by-product are extracted into the aqueous layer, and accordingly, a highly pure N-(α-alkoxyethyl)carboxylic acid amide can be obtained from the organic layer only by distillation under a reduced pressure.

Nevertheless, since the N-(α-alkoxyethyl)carboxylic acid amide synthesized by using an aliphatic alcohol having 1 to 4 carbon atoms as the starting alkanol has a high water solubility, a loss of the product into the aqueous layer is observed, and therefore, the distillation method is advantageous from the viewpoint of the isolation yield. The distillation method is defective, however, in that, since the boiling point of the carboxylic acid amide formed as the by-product is close to that of the intended N-(α-alkoxyethyl)carboxylic acid amide, separation is difficult.

Where an aliphatic alcohol having 5 to 10 carbon atoms or an alicyclic alcohol is used as the alkanol since the oil solubility of the intended N-(α-alkoxyethyl)carboxylic acid amide is relatively high, the intended product can be recovered by extraction. More specifically, after completion of the reaction, the acid catalyst is neutralized if necessary, and when water is added to the reaction mixture, since the mutual solubility between water and the alkanol having 5 to 10 carbon atoms is low, the reaction mixture is promptly separated into two layers, i.e., an aqueous layer and an alkanol layer.

The intended N-(α-alkoxyethyl)carboxylic acid amide is present in the alkanol layer, and there is no substantial loss into the aqueous layer. Furthermore, since the unreacted ethylidene-bisamide and the carboxylic acid amide formed as the by-product have a high water solubility, they are substantially transferred into the aqueous layer. If extraction with water is repeated according to need, an N-(α-alkoxyethyl)carboxylic acid amide having a high purity can be obtained. Also, in this case, since the water solubility of the N-(α-alkoxyethyl)carboxylic acid amide having an alkoxyl group having 5 to 10 carbon atoms is very low, there is no substantial loss of the intended product into the aqueous layer.

If the alkanol layer obtained in the above-mentioned manner is concentrated, a substantially pure N-(α-alkoxyethyl)carboxylic acid amide can be obtained. Of course, a method can be adopted in which the reaction mixture is first concentrated before the addition of water, and then water is added and the extraction carried out. When an N-(α-alkoxyethyl)carboxylic acid amide having a further improved purity is desired, this can be accomplished by carrying out a distillation under a reduced pressure after extraction and concentration. As the extraction solvent, there can be mentioned not only the alkanol used as the starting reaction material but also other organic solvents, but from the economical viewpoint, preferably the alkanol is directly used as the extraction solvent or the alkanol and another organic solvent are used in combination.

The ethylidene-bisamide and carboxylic acid amide are recovered from the aqueous layer obtained by the extraction by means such as concentration or crystallization and are reused for the reaction.

The ethylidene-bisamide has a high boiling point and it is difficult to recover the ethylidene-bisamide by distillation. Accordingly, the extraction with water is a very effective method of recovering the ethylidene-bisamide.

Where an aliphatic alcohol having 4 to 6 carbon atoms is used as the alkanol, since the boiling point of the intended N-(α-alkoxyethyl)carboxylic acid amide is relatively low and differs greatly from the boiling point of the carboxylic acid amide formed as the by-product, a very pure N-(α-alkoxyethyl)carboxylic acid amide can be obtained by distillation.

The N-(α-alkoxyethyl)carboxylic acid amide obtained according to the process of the present invention is mainly used as the intermediate for the preparation of, for example, an N-vinylcarboxylic acid amide, and this compound can be converted to a water-soluble polymer or a valuable chemical, as pointed out hereinbefore.

The conversion to the corresponding N-vinylcarboxylic acid amide can be accomplished by the reaction of eliminating the alkanol by heat decomposition. The eliminated alcanol can be easily recovered and reused for the reaction with the ethylidene-bisamide. The material to be subjected to heat decomposition need not be a very pure product as obtained by distillation, and the alkanol layer or organic layer obtained by extraction or a concentrate thereof can be directly used as the material to be subjected to heat decomposition.

The present invention will now be described in detail with reference to the following examples, that by no means limit the scope of the invention.

EXAMPLE 1

A 200-ml three-neck flask equipped with a thermometer and a Dimroth reflux condenser was charged with 14.4 g (0.1 mole) of ethylidene-bisacetamide, 88.15 g (1.0 mole) of n-amyl alcohol and 11.4 mg of concentrated sulfuric acid, the mixture was heated at 140° C., and a reaction was carried out for 5 hours. The catalyst was neutralized and a determination was carried out by gas chromatography, and it was found that the conversion of ethylidene-bisacetamide was 74.5% and the selectivity to N-(α-n-amyloxyethyl)acetamide was 85.5%.

EXAMPLE 2

A reaction was carried out at 140° C. in the same manner as described in Example 1 except that the amount of n-amyl alcohol was changed to 44.08 g (0.5 mole) and the amount of concentrated sulfuric acid was changed to 5.9 mg. After 5 hours, the catalyst was neutralized and a determination was carried out by the gas chromatography, and it was found that the conversion of ethylidene-bisacetamide was 58.0% and the selectivity to N-(α-n-amyloxyethyl)acetamide was 88.3%.

Water was added to the reaction mixture and extraction was carried out. When extraction with 100 ml of water was conducted 4 times, ethylidene-bisamide and acetamide were not observed in the organic layer (the analysis was conducted by gas chromatography). The amount of N-(α-n-amyloxyethyl)acetamide contained in the organic layer was 8.77 g (0.051 mole). The loss of N-(α-n-amyloxyethyl)acetamide at the extraction operation was 1.0%. The organic layer was concentrated by an evaporator to obtain 9.28 g of N-(α-n-amyloxyethyl)acetamide having a purity of 94.5%.

EXAMPLE 3

A reaction was carried out in the same manner as described in Example 2 except that the reaction temperature was changed to 120° C. After 2 hours, the catalyst was neutralized and a determination was carried out by the gas chromatography, and it was found that the conversion of ethylidene-bisacetamide was 40.3% and the selectivity to N-(α-n-amyloxyethyl)acetamide was 93.2%.

EXAMPLE 4

(Separation of N-(α-n-amyloxyethyl)acetamide by Distillation)

A reaction was carried out in the same manner as described in Example 1. The reaction mixture was neutralized and cooled to 5° C. Since unreacted ethylidene-bisacetamide was precipitated, the precipitate was removed by filtration and the filtrate was subjected to distillation under reduced pressure If the bath temperature was maintained at 90° C. under 1.0 mmHg, unreacted n-amyl alcohol and acetamide and di-n-amylacetal as the reaction by-products were distilled off, and 11.3 g of the residue was obtained When the residue was analyzed, it was found that the residue was N-(α-n-amyloxyethyl)acetamide having a purity of 95.2%.

The residue was further subjected to distillation under 1.0 mmHg at a bath temperature of 105° C. to obtain 10.2 g of a fraction boiling at 94.3° to 96.6° C. This fraction was pure N-(α-n-amyloxyethyl)acetamide.

EXAMPLE 5

A reaction was carried out in the same manner as described in Example 1 except that 10.2 mg of methanesulfonic acid was used as the catalyst. It was found that the conversion of ethylidene-bisacetamide was 75.5% and the selectivity to N-(α-n-amyloxyethyl)acetamide was 88.2%.

EXAMPLE 6

By using 5.2 mg of concentrated sulfuric acid, 37.05 g (0.5 mole) of n-butyl alcohol was reacted with 14.4 g (0.1 mole) of ethylidene-bisacetamide at 115° C. for 5 hours. The catalyst was neutralized and the reaction mixture was analyzed. It was found that the conversion of ethylidene-bisacetamide was 59.6% and the selectivity to N-(α-n-butoxyethyl)acetamide was 86.0%.

EXAMPLE 7

A reaction was carried out in the same manner as described in Example 1 except that 100.30 g (1.0 mole) of n-hexyl alcohol was used instead of n-amyl alcohol and the amount of concentrated sulfuric acid was changed to 13.3 mg. The reaction temperature was 157° C. After 5 hours, the catalyst was neutralized and the reaction mixture was analyzed It was found that the conversion of ethylidene-bisacetamide was 80.6% and the selectivity to N-(α-n-hexyloxyethyl)acetamide was 90.1%.

EXAMPLE 8

A three-neck flask (300 ml) equipped with a thermometer and a Dimroth reflux condenser was charged with 11.52 g (0.08 mole) of ethylidene-bisacetamide, 144 g (2.4 moles) of isopropyl alcohol and 0.078 g of concentrated sulfuric acid, the mixture was heated at 70° C., and a reaction was carried out for 3 hours. The catalyst was neutralized and a determination was carried out by gas chromatography, and it was found that the conversion of ethylidene-bisacetamide was 71% and the selectivity to N-(α-isopropoxyethyl)acetamide was 87%. Isopropyl alcohol was removed from the reaction mixture by distillation under a reduced pressure, chloroform (200 ml) and water (50 ml) were added to the residue, and the mixture was thoroughly shaken to extract N-(α-isopropoxyethyl)acetamide into the chloroform layer. When chloroform was removed by distillation under a reduced pressure, very pure N-(α-isopropoxyethyl)acetamide (6.25 g) was obtained in the form of a viscous liquid. The yield was 58% based on charged ethylidene-bisacetamide.

EXAMPLE 9

A reaction was carried out in the same manner as described in Example 8 except that the reaction temperature was changed to 82.5° C. After 30 minutes from the start of the reaction, aliquot of the reaction mixture was sampled and neutralized and a determination was carried out by gas chromatography, and it was found that the conversion of ethylidene-bisacetamide was 68% and the selectivity to N-(α-isopropoxyethyl)acetamide was 84.5%.

The reaction was further conducted, and after 3 hours, the reaction mixture was analyzed. It was found that the conversion of ethylidene-bisacetamide increased to 75% but the selectivity to N-(α-isopropoxyethyl)acetamide dropped to 71%.

EXAMPLE 10

A reaction was carried out in the same manner as described in Example 9 except that 36.0 g (0.6 mole) of isopropyl alcohol and 0.025 g of concentrated sulfuric acid were used. The ethylidene-bisacetamide/isopropyl alcohol molar ratio was 1/7.5. After 5 hours, a determination was carried out and it was found that the conversion of ethylidene-bisacetamide was 55% and the selectivity to N-(α-isopropoxyethyl)acetamide was 85%.

EXAMPLE 11

A reaction was carried out in the same manner as described in Example 8 except that 110.4 g (2.4 moles) of ethanol was used instead of isopropyl alcohol and the reaction temperature was changed to 78° C. After 1 hour, a determination was carried out and it was found that the conversion of ethylidene-bisacetamide was 65% and the selectivity to N-(α-ethoxyethyl)acetamide was 85%.

EXAMPLE 12

A reaction was carried out in the same manner as described in Example 8 except that 38.4 g (1.2 moles) of methanol was used instead of isopropyl alcohol and the reaction temperature was changed to 67° C. After 2 hours, a determination was carried out and it was found that the conversion of ethylidene-bisacetamide was 45% and the selectivity to N-(α-methoxyethyl)acetamide was 80%.

EXAMPLE 13

A reaction was carried out in the same manner as described in Example 8 except that 1.56 g of a strongly acidic cation exchange resin, "Amberlyst 15 (H+ type)" (trademark for the product supplied by Rhom & Haas), was used instead of concentrated sulfuric acid. After 5 hours, a determination was carried out and it was found that the conversion of ethylidene-bisacetamide was 76% and the selectivity to N-(α-isopropoxyethyl)acetamide was 75%.

EXAMPLE 14

A reaction was carried out in the same manner as described in Example 1 except that 88.20 g (1.0 mole) of isoamyl alcohol was used instead of n-amyl alcohol. The reaction temperature was 133° C. It was found that the conversion of ethylidene-bisacetamide was 78.1% and the selectivity to N-(α-i-amyloxyethyl)acetamide was 85.0%.

EXAMPLE 15

A reaction was carried out in the same manner as described in Example 2 except that 64.17 g (0.5 mole) of 2-ethylhexanol was used instead of n-amyl alcohol and the amount of concentrated sulfuric acid was changed to 8.1 mg. The reaction temperature was 145° C. After 5 hours, the catalyst was neutralized and the reaction mixture was analyzed, and it was found that the conversion of ethylidene-bisacetamide was 74.1% and the selectivity to N-(α-2-ethylhexyloxyethyl)acetamide was 91.2%.

EXAMPLE b 16

A reaction was carried out in the same manner as described in Example 2 except that 11.6 g (0.1 mole) of ethylidene-bisformamide was used instead of ethylidene-bisacetamide. It was found that the conversion of ethylidene-bisformamide was 60.3% and the selectivity to N-(α-n-amyloxyethyl)formamide was 92.0%.

EXAMPLE 17

A reaction was carried out in the same manner as described in Example 2 except that 17.2 g (0.1 mole) of ethylidene-bispropionamide was used instead of ethylidene-bisacetamide. It was found that the conversion of ethylidene-propionamide was 61.5% and the selectivity to N-(α-n-amyloxyethyl)propionamide was 90.5%.

EXAMPLE 18

A reaction was carried out in the same manner as described in Example 11 except that 21.4 g (0.08 mole) of ethylidene-bisbenzamide was used instead of ethylidene-bisacetamide and 1.56 g of a strongly acidic cation exchange resin, "Amberlyst 15 (H+ type)" (tradename for the product supplied by Rhom & Haas), was used as the catalyst. After 3 hours, a determination was carried out by liquid chromatography and it was found that the conversion of ethylidene-bisbenzamide was 85% and the selectivity to N-(α-ethoxyethyl)benzamide was 80%.

EXAMPLE 19

A reaction was carried out in the same manner as described in Example 18 except that 23.7 g (0.08 mole) of ethylidene-bis(α-phenyl)acetamide was used instead of ethylidene-bisbenzamide. It was found that the conversion of ethylidene-bis(α-phenyl)acetamide was 80% and the selectivity to N-(α-ethoxyethyl)-α-phenylacetamide was 81%.

As apparent from the foregoing description, according to the present invention, a high-purity N-(α-alkoxyethyl)carboxylic acid amide, which is valuable as an intermediate for the production of an N-vinylcarboxylic acid amide and the like, can be easily prepared from cheap and easily available starting materials.

We claim:

1. A process for the preparation of an N-(α-alkoxyethyl)carboxylic acid amide represented by the following formula [I]:

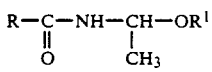

wherein R stands for a hydrogen atom, an alkyl group having 1 to 6 carbon atoms, a benzyl group or an aryl group, and $R^1$ stands for an alkyl group having 1 to 10 carbon atoms or a cycloalkyl group, which comprises reacting an ethylidene-bisamide represented by the following formula [II]:

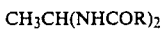

wherein R stands for a hydrogen atom, an alkyl group having 1 to 6 carbon atoms, a benzyl group or an aryl group, with an alkanol in the presence of an acid catalyst.

2. A process according to claim 1, wherein the alkanol is an aliphatic alcohol having 1 to 10 carbon atoms or an alicyclic alcohol.

3. A process according to claim 1, wherein the alkanol is an aliphatic alcohol having 5 to 10 carbon atoms or an alicyclic alcohol, and the process comprises, after the reaction, adding water to the reaction mixture to separate the formed N-(α-alkoxyethyl)carboxylic acid amide from the unreacted ethylidene-bisamide and carboxylic acid amide formed as the by-product.

4. A process according to claim 1, wherein the alkanol is an aliphatic alcohol having 1 to 6 carbon atoms or an alicyclic alcohol, and the process comprises, after the reaction, separating and purifying the N-(α-alkoxyethyl)carboxylic acid made of the formula (I) by distillation.

5. A process according to claim 1, wherein R in the formula [II] is a methyl group.

6. A process according to claim 5, wherein the alkanol is n-butanol or n-amyl alcohol.

* * * * *